United States Patent
Cho et al.

(10) Patent No.: US 8,258,272 B2
(45) Date of Patent: *Sep. 4, 2012

(54) AGENT FOR CONTROLLING BCL-2 EXPRESSION COMPRISING GINSENOSIDE F1 AS AN ACTIVE COMPONENT

(75) Inventors: Si-Young Cho, Yongin-si (KR); Eun-Hee Lee, Yongin-si (KR); Su-Jung Kim, Yongin-si (KR); Eui-Seok Shin, Yongin-si (KR); Hui-Kyoung Chang, Yongin-si (KR); Duck-Hee Kim, Seoul (KR); Myeong Hoon Yeom, Yongin-si (KR); Kwang-Sik Woe, Chungju-si (KR); Tae-Ryong Lee, Suwon-si (KR); Young-Chul Sim, Seongnam-si (KR)

(73) Assignee: Amorepacific Corporation, Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 12/135,663

(22) Filed: Jun. 9, 2008

(65) Prior Publication Data

US 2008/0261899 A1    Oct. 23, 2008

Related U.S. Application Data

(63) Continuation of application No. 10/539,012, filed as application No. PCT/KR03/02859 on Dec. 27, 2003, now abandoned.

(30) Foreign Application Priority Data

Dec. 28, 2002 (KR) .................. 10-2002-0085716

(51) Int. Cl.
*A61K 31/704* (2006.01)
*A61P 17/00* (2006.01)
*C07J 17/00* (2006.01)

(52) U.S. Cl. .......................................... 536/5

(58) Field of Classification Search .................. None
See application file for complete search history.

(56) References Cited

U.S. PATENT DOCUMENTS 5,776,460 A * 7/1998 Kim et al. .............. 424/728
6,261,603 B1 * 7/2001 McElwain ............. 424/522

FOREIGN PATENT DOCUMENTS

EP    1327434 A1 *   7/2003
KR    2003-37005 A    5/2003
KR    2003-60017 A    7/2003
KR    2003-94523 A   12/2003

OTHER PUBLICATIONS

Chen Xiao-Chun et al., Acta Pharmacol Sin, Protective effect of ginsenoside Rg1 on dopamine-induced apoptosis in PC12 cells, (2001), vol. 8, pp. 673-678.*
Lee Enn Hee et al., Journal of Investigative Dermatology, Ginsenoside F1 Protects Human HaCaT Keratinocytes from Ultraviolet-B-Induced Apoptosis by Maintaining Constant Levels of Bcl-2, (2003), vol. 121, issue 3, pp. 607-613.*
Edited by Mazza, G. and Oomah, B.D.; Herbs, Botanicals, and Teas: Kitts, D.D., Chapter 2: Chemistry and Pharmacology of Ginseng and Ginseng Products (2000), select pages provided.*
Date of Herbs, Botanicals, and Teas on Google.com, last viewed Jul. 13, 2009, publication date of book 2000, http://www.google.com/search?sourceid=navclient&ie=UTF-8&oe=UTF-8&q=ginsenoside+rg1%2C+beverage.*
Merck Manual Online Medical Library; "skin cancer prevention", also available at http://www.merck.com/mmpe/sec10/ch128/ch128a.html?qt=skin%20cancer&alt=sh#sec10-ch128-ch128a-1176c; last viewed Feb. 18, 2010.*
American Academy of Dermatology, AgingSkinNet "Causes of Aging Skin"; also available at http://www.skincarephysicians.com/agingskinnet/basicfacts.html; last viewed Feb. 18, 2010.*
WordNet 3.0 "prevent"; also available at http://wordnetweb.princeton.edu/perl/webwn; last viewed Nov. 14, 2007.*
Uvarova et al., Pharmaceutical Chemistry Journal, Medicinal Plants "Triterpene Glycosides From Wild and Cultivated Ginseng Occurring in Maritime Territory: Chemical Characterization, Comparative Quantitative Analysis, and Biological Activity Study", vol. 34, issue 3 (2000).*
Yeom, M. H. et al., Cosmetics & Toiletries, "Anti-wrinkle activity of hydrolyzed ginseng saponins", May 2003, vol. 118, No. 3, pp. 77-80 and 82.*

(Continued)

*Primary Examiner* — Shaojia Anna Jiang
*Assistant Examiner* — Bahar Schmidtmann
(74) *Attorney, Agent, or Firm* — Sughrue Mion, PLLC (57) ABSTRACT

The present invention relates to an agent for controlling Bcl-2 expression comprising ginsenoside F1 (20-O-β-D-glucopyranosyl-20(S)-protopanaxatriol) represented by the following formula 1 as an active component.

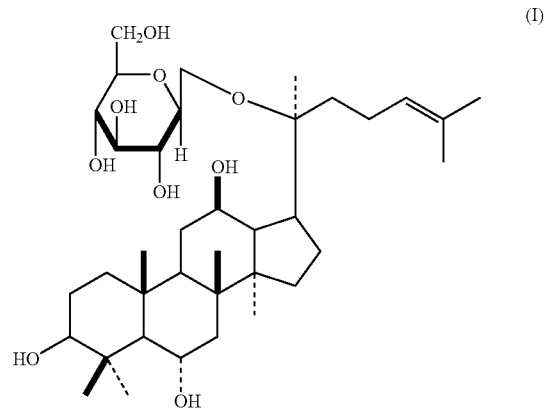

(I)

3 Claims, 6 Drawing Sheets

OTHER PUBLICATIONS

Greul et al., Skin Pharmacology and Applied Skin Physiology, Photoprotection of UV-Irradiated Human Skin: An Antioxidative Combination of Vitamins E and C, Carotenoids, Selenium and Proanthocyanidins, Sep./Oct. 2002, vol. 15, issue 5, pp. 307-315.*

Zhang, You-wei, et al., "Effect of ginsenosides from Panax ginseng on proliferation of human osteosarcoma cell U2OS," Chinese Traditional and Herbal Drugs, vol. 32, No. 3, 2001, pp. 232-236.

Zhang, You-wei, et al., "Effects of ginsenosides from Panax ginseng on cell-to-cell communication function mediated by gap junctions," Plata Med., vol. 67, No. 5, Jul. 2001, pp. 417-422.

Lee, E.H. et al., "Ginsenoside F1 protects human HaCaT keratinocytes from ultraviolet-B-induced apoptosis by maintaining constant levels of Bcl-2", Journal of Invest. Dermatol., vol. 121, No. 3, Sep. 2003, pp. 607-613.

Ko, S.R., et al., "Enzymatic preparation of ginsenosides Rg2,Rh1, and F1", Chem. Pharm. Bull. (Tokyo), vol. 51, No. 4, Apr. 2003, pp. 404-408.

Smith, Martin D., et al., "Bcl-2 Transcription from the Proximal P2 Promoter Is Activated in Neuronal Cells by the Brn-3a POU Family Transcription Factor," The Journal of Biological Chemistry, vol. 273, No. 27, Issue of Jul. 3, 1998, pp. 16715-16722.

Hockenbery, David W., et al., "BCL2 protein is topographically restricted in tissues characterized by apoptotic cell death," Pro. Natl. Acad. Sci. USA, vol. 88, Aug. 1991, pp. 6961-6965.

Rodriguez-Villanueva, J., et al., "The expression and localization of bcl-2 protein in normal skin and in non-melanoma skin cancers," Pathol. Res. Pract., vol. 191, No. 5, Jun. 1995, pp. 391-398.

Sermadiras, S., et al., "Expression of Bcl-2 and Bax in cultured normal human keratinocytes and melanocites: relationship to differentiation and melanogenesis," Br. J. Dermatol., vol. 137, No. 6, Dec. 1997, pp. 883-889.

Fisher, Gary J., et al., "Pathophysiology of Premature Skin Aging Inducted by Ultraviolet Light," The New England Journal of Medicine, vol. 337, No. 20, Nov. 13, 1997, pp. 1419-1428.

Takahashi, H., et al., "In Vitro and In Vivo Transfer of bcl-2 Gene into Keratinocytes Suppresses UVB-induced Apoptosis," Photochemistry and Photobiology, vol. 74, No. 4, 2001, pp. 579-586.

* cited by examiner

Untreated

Ginsenoside F1

Untreated + UVB

Ginsenoside F1 + UVB

SEQUENCE LISTING

<160> NUMBER OF SEQ ID NOS: 4

<210> SEQ ID NO 1
<211> LENGTH: 22
<212> TYPE: DNA
<213> ORGANISM: Artificial Sequence
<220> FEATURE:
<223> OTHER INFORMATION: Bcl-2 forward primer

```
<400> SEQUENCE: 1
tacgataacc gggagatagt ga                                    22

<210> SEQ ID NO 2
<211> LENGTH: 20
<212> TYPE: DNA
<213> ORGANISM: Artificial Sequence
<220> FEATURE:
<223> OTHER INFORMATION: Bcl-2 reverse Primer

<400> SEQUENCE: 2
caggtgccgg ttcaggtact                                       20

<210> SEQ ID NO 3
<211> LENGTH: 23
<212> TYPE: DNA
<213> ORGANISM: Artificial Sequence
<220> FEATURE:
<223> OTHER INFORMATION: GAPDH forward primer

<400> SEQUENCE: 3
caactacatg gtttacatgt tcc                                   23

<210> SEQ ID NO 4
<211> LENGTH: 20
<212> TYPE: DNA
<213> ORGANISM: Artificial Sequence
<220> FEATURE:
<223> OTHER INFORMATION: GAPDH reverse primer

<400> SEQUENCE: 4
ggactgtggt catgagtcct                                       20
```

AGENT FOR CONTROLLING BCL-2 EXPRESSION COMPRISING GINSENOSIDE F1 AS AN ACTIVE COMPONENT

This is a Continuation Application of U.S. Ser. No. 10/539,012 filed on Apr. 27, 2006 now abandoned, which is a National Stage Application under 35 U.S.C. §371 of PCT/KR2003/002859 filed on Dec. 27, 2003, which claim benefit from Korean Patent Application 10-2002-0085716 filed Dec. 28, 2002, all of which are incorporated herein by reference.

FIELD OF THE INVENTION

The present invention relates to an agent for controlling Bcl-2 expression comprising ginsenoside F1 (20-O-β-D-glucopyranosyl-20(S)-protopanaxatriol) represented by the following formula 1 as an active component.

[Formula 1]

BACKGROUND OF THE INVENTION

Ultraviolet radiation is a part of solar rays with 200-400 nm of wavelength and is a part of the electromagnetic spectrum; especially UVB (Ultraviolet-B) with 280-320 nm of wavelength is the major part of the ultraviolet radiation to cause skin aging leading to skin-burn and skin cancer. When the skin is exposed to ultraviolet radiation, DNA, proteins, lipids, etc., in cells are damaged and thereby generate sunburn-cells. These sunburn-cells undergo apoptosis, accompanied by DNA fragmentation, activation of caspase, and the like. High-dose radiation on the cell causes serious DNA damages that are not recovered from; and the apoptosis prevents the cell from developing to a tumor by inducing the cell to die. Therefore, in order to prevent cancer and maintain cell homeostasis, it is very important to induce or to prevent apoptosis of the cell selectively according to the degree of cell damages.

Bcl-2 plays a very important role in the process of apoptosis of the skin cell. The Bcl-2 gene encodes 26 kDa protein present in a nuclear membrane and an outer membrane of mitochondria. Bcl-2 is a protein that inhibits apoptosis of a cell by adhering to a protein such as Bax, which accelerates the apoptosis, to inhibit its function. Therefore, apoptosis of a cell can be determined by the concentration ratio of Bcl-2 and Bax.

UVB irradiation has been known to decrease Bcl-2 expression of human keratinocyte. Furthermore, Bcl-2-transfected HaCaT cells or Bcl-2-overexpressing transgenic mice were shown to be resistant to UVB-induced apoptosis. However, over-expression of Bcl-2 prevents apoptosis of a cell with serious DNA damage and thereby causes a cancer. Therefore, it is very important to control the expression of Bcl-2 selectively.

Up to now, techniques or methods for controlling the expression of Bcl-2 have not been widely disclosed compared with the functions of Bcl-2. Only some transcription factors such as pRb, c-myb and Brn-3a in nerve cells have been disclosed. In particular, it is reported that Brn-3a, a type IV POU domain transcription factor, adheres to a P2 promoter of Bcl-2 and controls the expression of a Bcl-2 gene to protect the nerve cells from apoptosis.

However, mechanisms or factors to control the expression of Bcl-2 in HaCaT cells derived from human skin have not yet been disclosed.

In addition, a material for controlling the expression of Bcl-2 that is not toxic and is easily applied to the human body have not yet been disclosed.

SUMMARY OF THE INVENTION

Under theses circumstances, the present inventors found that ginsenoside F1, which obtained from purified ginseng saponin, protects human HaCaT cells from UVB-induced apoptosis by maintaining constant levels of Bcl-2. That is, the present inventors found that ginsenoside F1 controls the expression of Bcl-2 and thereby inhibits the apoptosis of cells, and so accomplished the present invention.

Therefore, an object of the present invention is to provide an agent for controlling Bcl-2 expression comprising ginsenoside F1 as an active component.

Another objection of the present invention is to provide a promoter or an inhibitor of apoptosis comprising ginsenoside F1 as an active component.

DETAILED DESCRIPTION OF THE PRESENT INVENTION

The present invention provides an agent for controlling Bcl-2 expression comprising ginsenoside F1 represented by the following formula 1 as an active component.

[Formula 1]

Ginsenoside F1 protects these cells against low-dose radiation of UVB-induced apoptosis by maintaining constant levels of Brn-3a and the corresponding inhibition of Bcl-2 downregulation. That is, ginsenoside F1 itself does not promote the Bcl-2 expression, but inhibits the downregulation of Bcl-2 caused by ultraviolet radiation. On the contrary, under the high-dose radiation of ultraviolet rays, it induces the decrease of Bcl-2 expression to promote apoptosis.

In conclusion, ginsenoside F1 inhibits the decrease of Bcl-2 expression under low-dose radiation of ultraviolet rays resultingly to prevent apoptosis of cells; however induces apoptosis under the high-dose radiation of ultraviolet rays, on the contrary; and thereby prevents skin cancer. Therefore, ginsenoside F1 may be used as an anti-aging material inhibiting cell damages.

The present invention confirmed that ginsenoside F1 controls the expression of Brn-3a, a transcription factor of Bcl-2, and thereby can maintain the degree of Bcl-2 expression to a normal level.

Therefore, ginsenoside F1 can prevent apoptosis by maintaining the degree of Bcl-2 expression in a cell to desirable level. However, ginsenoside F1 itself does not promote the Bcl-2 expression. These show that ginsenoside F1 has the efficacies of preventing apoptosis and cell damages caused by the radiation of ultraviolet rays without generating skin cancer.

BRIEF DESCRIPTION OF THE DRAWINGS

FIG. 2A-D shows the changes of shapes of the cells, wherein cells treated with ginsenoside F1 and exposed to ultraviolet radiation were compared with a control untreated with ginsenoside F1.

FIG. 3A(a-d) shows the degrees of DNA fragmentation of cells, wherein cells treated with ginsenoside F1 and exposed to ultraviolet radiation were compared with a control untreated with ginsenoside F1.

FIGS. 4A and B shows the degrees of PARP segmentation in cells obtained from the result of Western blotting, wherein cells treated with ginsenoside F1 and exposed to ultraviolet radiation were compared with a control untreated with ginsenoside F1.

FIGS. 5A and B shows the degrees of Bcl-2 expression with mRNA level, wherein cells treated with ginsenoside F1 and exposed to ultraviolet radiation were compared with a control untreated with ginsenoside F1.

PREFERRED EMBODIMENT OF THE INVENTION

Hereinafter, the present invention is described in detail with reference to examples. However, the scope of the present invention is not restricted by the examples.

REFERENCE EXAMPLE 1

Preparation of Purified Ginseng Saponin 2 kg of Red ginseng (KT&G Corporation, 6 year old red ginseng) was added into 4 l of methanol containing water, and refluxed 3 times then deposited for 6 days at 15° C. Residues and remainders were separated by filtration and centrifugation, then the remainders were concentrated under reduced pressure to obtain extract. The extract was suspended into the water and re-extracted with 1 l of ether 5 times to remove pigments, then water layer thereof was extracted with 500 ml of 1-butanol 3 times. The above-obtained 1-butanol layer was treated with 5% of KOH and washed with distilled water then concentrated under reduced pressure to obtain 1-butanol extract. The extract (1-butanol extract) was dissolved in a small amount of methanol, and a large amount of ethylacetate was added thereto to obtain precipitation. The precipitation was dried to obtain 70 g of purified ginseng saponin extract.

REFERENCE EXAMPLE 2

Preparation of Gensenoside F1

10 g of purified ginseng saponin obtained from the Reference Example 1 was dissolved in 1000 ml of citrate buffer solution (pH 4.0), 15 g of naringinase obtained from *penicillium* sp. was added thereto and reacted for 48 hours while stirring at 40° C. After the reaction, reaction mixture was heated for 10 minutes to inactivate the enzyme, then the reaction mixture was extracted 3 times with same amount of ethylacetae and concentrated. The product obtained underwent column chromatography (chloroform:methanol=9:1) and finally separated 1.5 g of ginsenoside F1.

EXAMPLE 1

Inhibition of Apoptosis of HaCaT Cells Induced by Ultraviolet Radiation, when Treated with Ginsenoside F1

<Step 1> Cell Line and Cell Culture

Human keratinocyte, HaCaT (obtained from Dr. Fusenig in German Cancer Research Center (DKFZ)) was cultured in Dulbecco's modified Eagle's Medium (DMEM; Gibco 1210-0038) containing 10% of fetal bovin serum at 37° C. and 5% of $CO_2$.

<Step 2> Inhibition of Apoptosis of Cells Induced by Ultraviolet Radiation, when Treated with Ginsenoside F1

Figure 1:
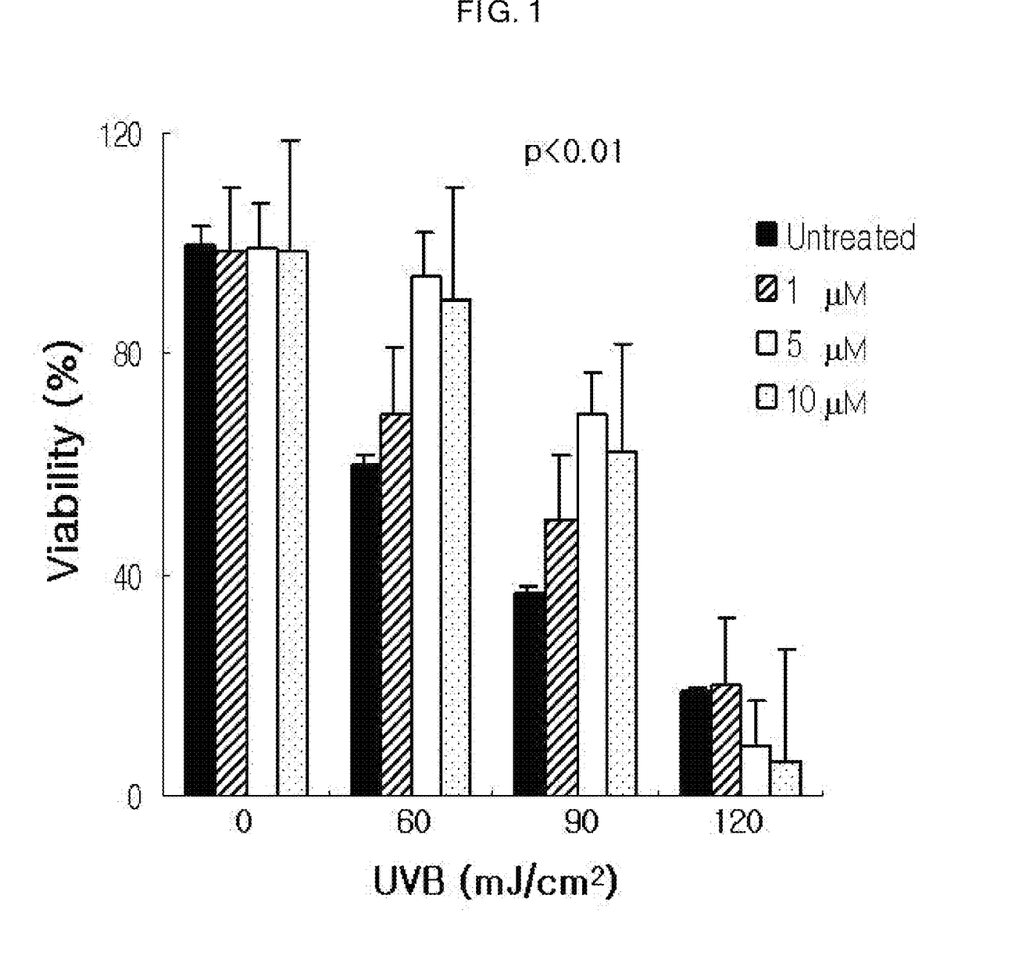
FIG. 1 is a graph showing viabilities of HaCaT skin cells obtained from the result of MTT assay, wherein cells treated with ginsenoside F1 and exposed to ultraviolet radiation were compared with a control (cells) untreated with ginsenoside F1.
Figure 2:
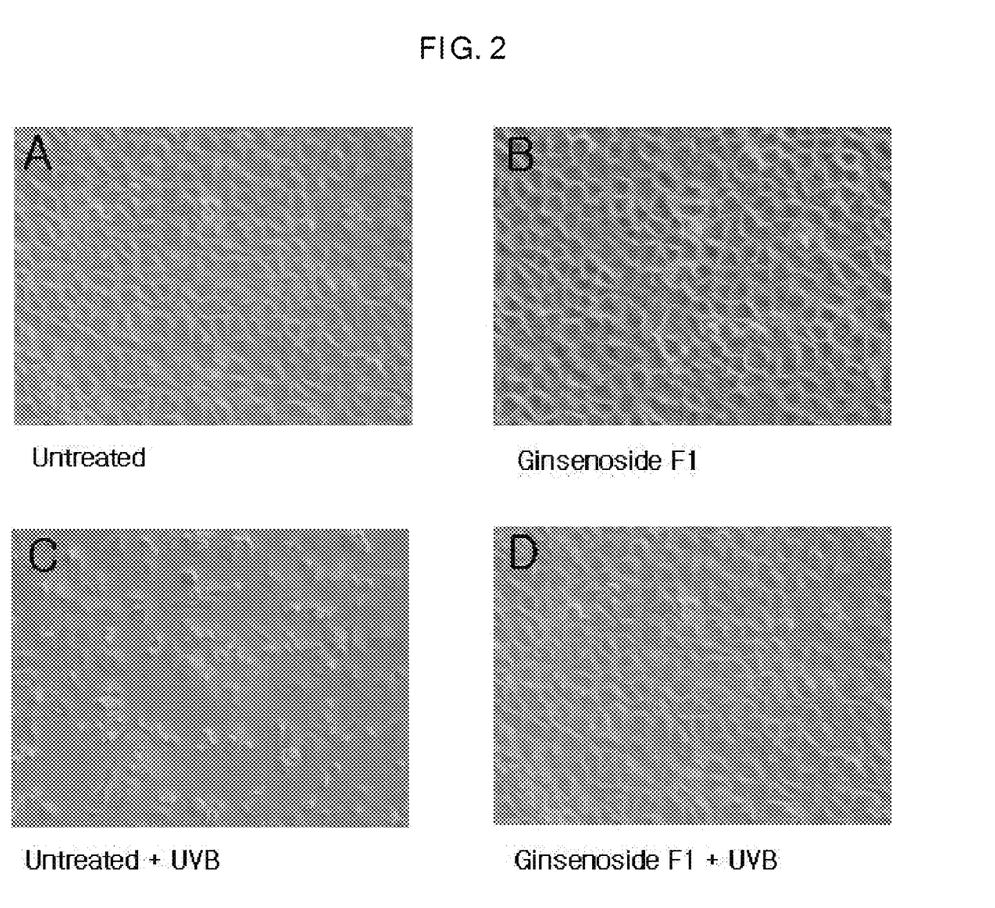

Cells cultured in step 1 were treated with trypsin to obtain single cell suspension, and seeded into 6-well flask with $2 \times 10^5$/well, then cultured for 24 hours. After that, the cells were cultured again in a new DMEM not containing fetal bovin serum for 24 hours, then treated with 1, 5, 10 μM of ginsenoside F1. Ginsenoside F1 was dissolved in 100% ethanol and added to be 1/1000 of the medium concentration. After 24 hours of treatment with ginsenoside F1, the cell cultures were washed with phosphate buffered saline (PBS), and exposed to 60-120 mJ/cm$^2$ of UVB radiation with a state containing PBS. Then, the PBS was removed and medium was changed with a fresh one containing the same concentration of ginsenoside F1. In addition, the cells untreated with ginsenoside F1 were cultured as a control. After 24 hours of UVB radiation, 3-[4,5-dimethyl tetrazole]-2,5-diphenyltetrazolium bromide (MTT, Sigma) was added to all the cells treated and untreated with ginsenoside F1, then cultured 4 hours at 37° C. After culture, the cells were dissolved with dimethylsulfoxide, then optical density (OD) of formazan dye generated at 540 nm was measured with ELISA reader (Thermo Max, Molecular Devices Co.). OD value of the cells not-exposed to the UVB was given 100%, then the relative values of the other cells were calculated and determined as viabilities thereof. The results are shown in FIG. 1. The cells treated with ginsenoside F1 showed 1.5 times more inhibition of apoptosis compared with those untreated, when exposed to the UVB. However, under the 120 mJ/cm² of UVB radiation, the cells treated with ginsenoside F1 showed more apoptosis than those untreated.

EXAMPLE 2

Inhibition of DNA Fragmentation of HaCaT Cells Induced by Ultraviolet Radiation, when Treated with Ginsenoside F1

<Step 1> Cell Line and Cell Culture

Same procedures of step 1 of Example 1 were performed.
<Step 2> Inhibition of DNA fragmentation of HaCaT cells induced by ultraviolet radiation, when treated with ginsenoside F1

Cells cultured in step 1 were treated with trypsin to obtain single cell suspension, and seeded into 6-well flask with $2\times10^5$/well, then cultured for 24 hours. After that the cells were cultured again in a new DMEM not containing fetal bovin serum for 24 hours, then treated with 5 μM of ginsenoside F1. After 24 hours of treatment with ginsenoside F1, the cultures were washed with phosphate buffered saline (PBS), and exposed to 60 mJ/cm² of UVB radiation with a state containing PBS. Then, the PBS was removed and medium was changed with a fresh one containing the same concentration of ginsenoside F1. In addition, the cells untreated with ginsenoside F1 were cultured as a control.

After 24 hours of UVB radiation, all the cells treated and untreated with ginsenoside F1 were washed with phosphate buffered saline (PBS), and treated with phosphate buffered saline containing 4% of paraformaldehyde for 15 minutes to fix the cells. Then the cells were washed with phosphate buffered saline (PBS), and reacted in phosphate buffered saline (PBS) containing 0.05% of tween 20 and 0.2% of BSA for 15 minutes. Terminal deoxynucleotide transferase reaction solution (TUNEL Apoptosis detection kit, Upstate, USA) was added thereto and reacted for 1 hour. Reaction termination buffer (TUNEL Apoptosis detection kit, Upstate, USA) was added to stop the reaction, and blocking solution (TUNEL Apoptosis detection kit, Upstate, USA) was added thereto, then reacted for 20 minutes. Avidin-FITC (TUNEL Apoptosis detection kit, Upstate, USA) was added thereto and reacted for 30 minutes, then washed with phosphate buffered saline.

Figure 3:
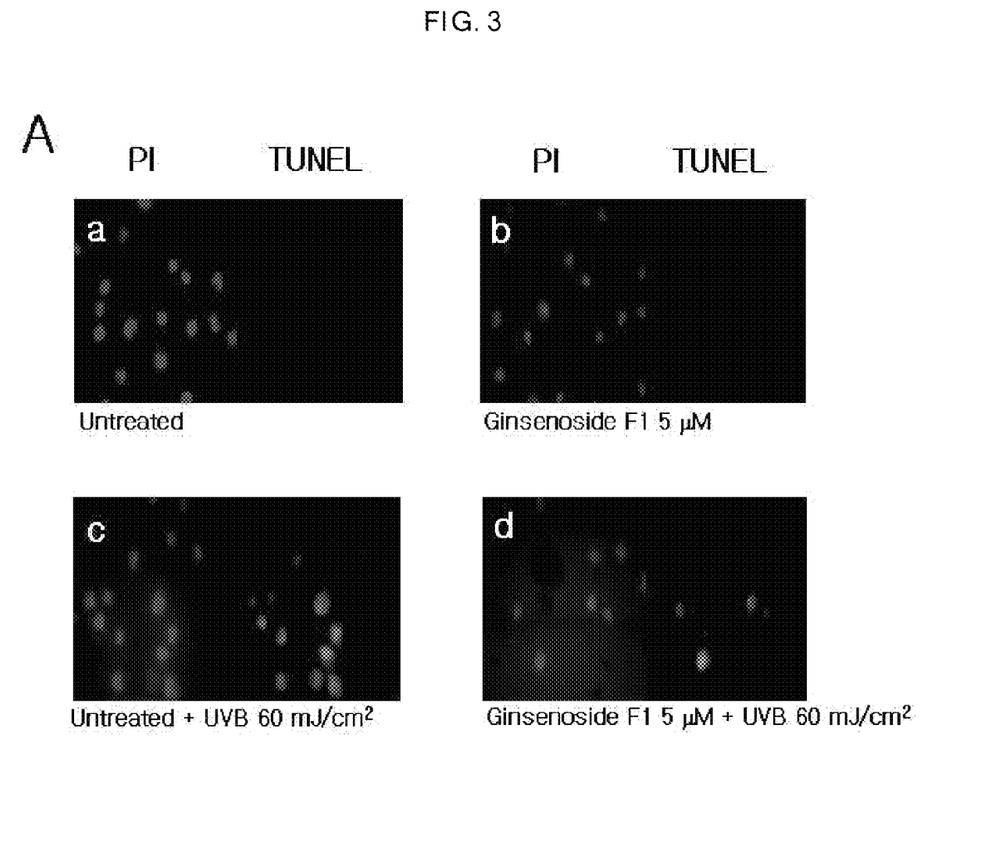

Counterstain was performed with 500 nM of propidium iodide solution and observed with microscope. By observing about 200 cells, the number of DNA fragmentation in the total cells was calculated. The cells treated with ginsenoside F1 showed 2.4 times decrease of DNA fragmentation compared with those untreated, when exposed to the UVB. The results are shown in FIG. 3.

EXAMPLE 3

Inhibition of PARP Protein Segmentation Induced by Ultraviolet Radiation, when Treated with Ginsenoside F1

<Step 1> Cell Line and Cell Culture

Same procedures of step 1 of Example 1 were performed.
<Step 2> Inhibition of PARP Protein Segmentation Induced by Ultraviolet Radiation, when Treated with Ginsenoside F1

Cells cultured in step 1 were treated with trypsin to obtain single cell suspension, and seeded into 6-well flask with $2\times10^5$/well, then cultured for 24 hours. After that the cells were cultured again in a new DMEM not containing fetal bovin serum for 24 hours, then treated with 5 μM of ginsenoside F1. After 24 hours of treatment with ginsenoside F1, the cell cultures were washed with phosphate buffered saline (PBS), and exposed to 60 mJ/cm² of UVB radiation with a state containing PBS. Then, the PBS was removed and medium was changed with a fresh one containing 5 μM of ginsenoside F1. In addition, the cells untreated with ginsenoside F1 were cultured as a control.

After 24 hours of UVB radiation, all the cell cultures treated and untreated with ginsenoside F1 were washed with phosphate buffered saline (PBS), and cells were collected by treating with trypsin, and which were treated with 8M of urea, 2% of CHAPS, 50 mM of DTT, 2M of thiourea, 2 mM of PMSF and 500 μl of protein extract buffer solution of 100 μg/ml leupeptine, then left at room temperature for 10 minutes; and then centrifuged with 15,000 g of gravity for 10 minutes at 4° C., and supernatant was collected then protein was quantitated with BIO-Rad Protein Dye Reagent™. 20 μg of protein was separated according to sizes thereof with 8% SDS-PAGE, and blotted on PDF (BioRad) membrane with 50V for 12 hours. The blots obtained were blocked with 5% of fat-free milk solution for 1 hour and performed Western blotting with enhanced chemiluminescence (ECL) kit of Amersham Bioscience by using polyclonal anti-PARP (Santa Cruz) as primary antibody and using anti-rabbit IgG (amersham) combined with horse radish peroxidase as secondary antibody.

Figure 4:
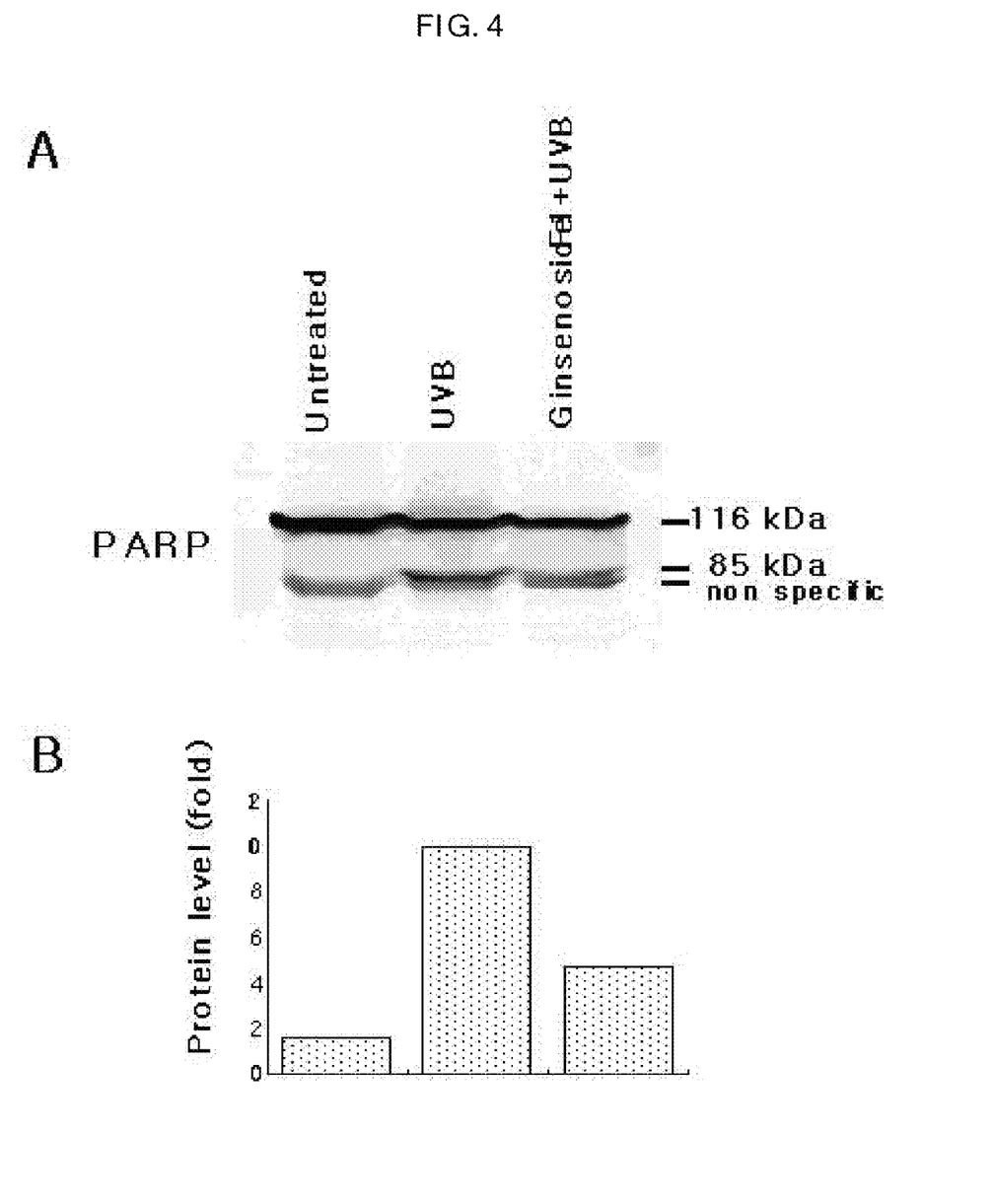

The blots reacted were exposed to X-ray Fuji film and developed to observe the degree of protein expression. Bands on the film were scanned with PowerLook 2100 XL (umax) and analyzed with an image-analyzing program of Image-Master 2D Elite (Amersham Bioscience). The amount of PARP protein segmentation was estimated with a relative value compared with that of control. The cells treated with ginsenoside F1 showed 1.4 times decrease of PARP protein segmentation compared with those untreated, when exposed to the UVB. The results are shown in FIG. 4.

EXAMPLE 4

Inhibition of Decrease of Bcl-2 Expression Induced by Ultraviolet Radiation, when Treated with Ginsenoside F1

<Step 1> Cell Line and Cell Culture

Same procedures of step 1 of Example 1 were performed.
<Step 2> Inhibition of Decrease of Bcl-2 Expression Induced by Ultraviolet Radiation, when Treated with Ginsenoside F1

Cells cultured in step 1 were treated with trypsin to obtain single cell suspension, and seeded into 6-well flask with $2\times10^5$/well then cultured for 24 hours. After that the cells were cultured again in a new DMEM not containing fetal bovin serum for 24 hours, then treated with 5 μM of ginsenoside F1. After 24 hours of treatment with ginsenoside F1, the cell cultures were washed with phosphate buffered saline (PBS), and exposed to 60 mJ/cm² of UVB radiation with a state containing PBS. Then, the PBS was removed and medium was changed with a fresh one containing 5 μM of ginsenoside F1. In addition, the cells untreated with ginsenoside F1 were cultured as a control.

After 24 hours of UVB radiation and excluding UVB radiation on a predetermined time interval, all the cell treated and untreated with ginsenoside F1 were washed with phosphate buffered saline (PBS), and mRNAs were extracted with Oligotex Direct mRNA kits (QIAGEN, Hilden, Germany) then performed quantitative reverse transcription PCR (RT-PCR). The sequences of Bcl-2 and glyceraldehydes-3-phosphate dehydrogenase (GAPDH) primer pairs to performed the quantitative RT-PCR of are shown in table 1.

TABLE 1

Bcl-2 and GAPDH primers to performed quantitative RT-PCR

| Primer | Sequence |
|---|---|
| Bcl-2 forward primer | 5'-TACGATAACCGGGAGATAGTGA-3' (nucleotides 56-77 of human Bcl-2 cDNA) |
| Bcl-2 reverse Primer | 5'-CAGGTGCCGGTTCAGGTACT-3' (nucleotides 566-586 of human Bcl-2 cDNA) |
| GAPDH forward primer | 5'-CAACTACATGGTTTACATGTTCC-3' (nucleotides 174-194 of human GAPDH cDNA) |
| GAPDH reverse primer | 5'-GGACTGTGGTCATGAGTCCT-3' (nucleotides 570-589 of human GAPDH cDNA) |

1 μg of mRNA was added to 25 μl of reverse transcription reaction buffer solution with 50 mM of Tris-HCl (pH 8.3), 75 mM of KCl, 3 mM of MgCl$_2$, 0.1M of DTT, 10 mM of dNTP and 40 units/ml of RNase inhibitor, then 0.5 μg/ml oligo (dT)$_{16}$ primer and 200 units of SuperScript II (GiboBRL) reverse transcription polymerase were added thereto and reacted for 1 hour at 42° C. 2.5 μl of reverse transcription reaction solution was mixed to 50 μl PCR buffer solution with 50 mM of KCl, 10 mM of tris-HCl (pH 8.3), 5 mM of MgCl$_2$ and 100 μM of dNTP, and 10 μM of primer and 0.5 U of Taq DNA polymerase were added thereto, then repeated 30 cycles of; 30 sec at 95° C., 30 sec at 58° C. and 30 sec at 72° C. PCR products were electrophoresed through agarose gels and scanned, then analyzed with the image-analyzing program of ImageMaster 2D Elite (Amersham Bioscience). The degree of Bcl-2 expression was estimated with a relative value compared with that of GAPDH.

Figure 5:
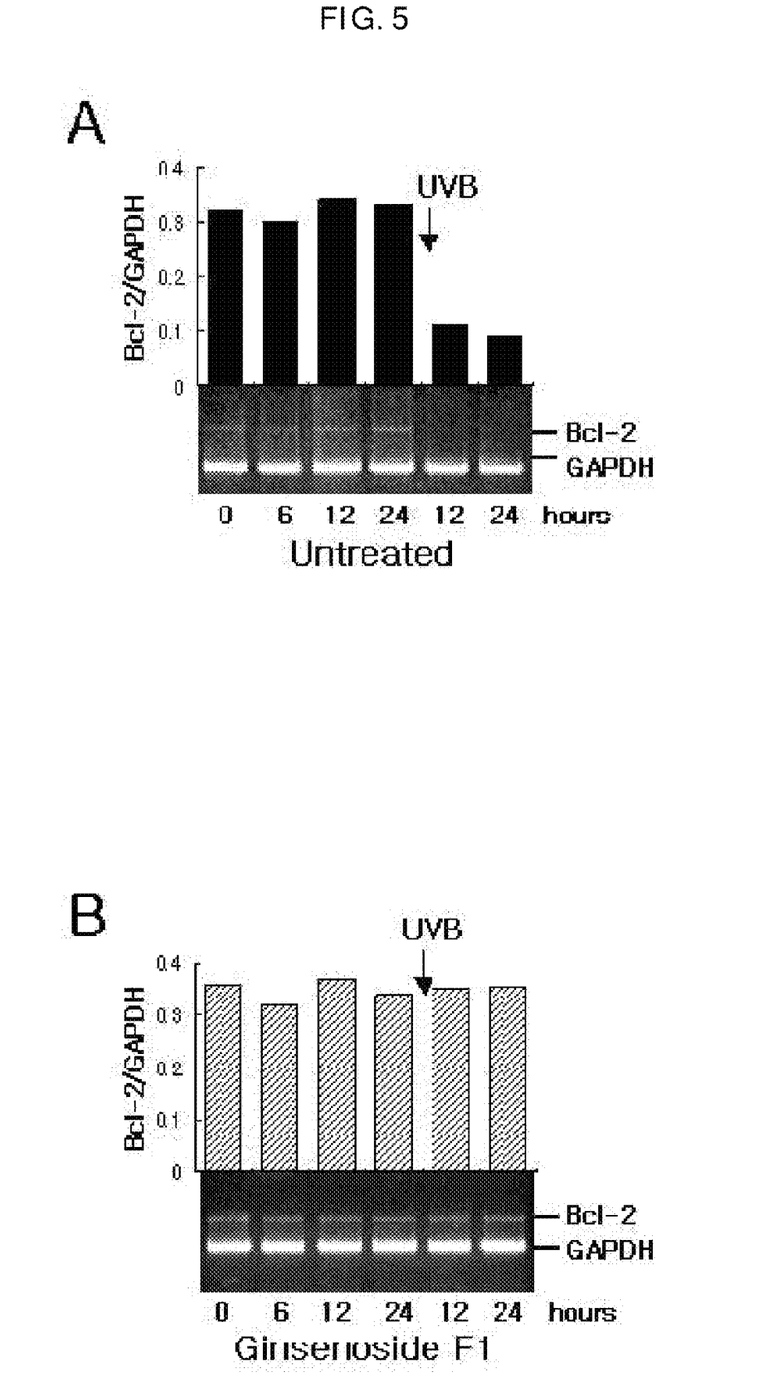

When cells were treated with ginsenoside F1 only, expression of Bcl-2 according to time-passage was not different from that of the cells untreated. When UVB was radiated, the expression of Bcl-2 in the cells untreated with ginsenoside F1 was decreased, and after 24 hours later Bcl-2 was hardly expressed. However, in the cells treated with ginsenoside F1, the expression of Bcl-2 was maintained almost the same even when UVB was radiated compared when UVB was not radiated. That is, when the cells were treated with ginsenoside F1, the expression of Bcl-2 increased 3 times compared with that untreated. The results are shown in FIG. 5.

EXAMPLE 5

Inhibition of Decrease of Brn-3a Expression Induced by Ultraviolet Radiation, when Treated with Ginsenoside F1

<Step 1> Cell Line and Cell Culture
Same procedures of step 1 of Example 1 were performed.
<Step 2> Inhibition of Decrease of Brn-3a Expression Induced by Ultraviolet Radiation, when Treated with Ginsenoside F1

Cells cultured in step 1 were treated with trypsin to obtain single cell suspension, and seeded into 6-well flask with 2×10$^5$/well, then cultured for 24 hours. After that the cells were cultured again in a new DMEM not containing fetal bovin serum for 24 hours, then treated with 5 μM of ginsenoside F1. After 24 hours of treatment with ginsenoside F1, the cell cultures were washed with phosphate buffered saline (PBS), and exposed to 60 mJ/cm$^2$ of UVB radiation with a state containing PBS. Then, the PBS was removed and medium was changed with a fresh one containing 5 μM of ginsenoside F1. In addition, the cells that are not treated with ginsenoside F1 were cultured as a control.

After 24 hours of UVB radiation, all the cell cultures treated and untreated with ginsenoside F1 were washed with phosphate buffered saline (PBS), and cells were collected by treating with trypsin, and which were treated with 8M of urea, 2% of CHAPS, 50 mM of DTT, 2M of thiourea, 2 mM of PMSF and 500 μl of protein extract buffer solution of 100 μg/ml leupeptine, then left at room temperature for 10 minutes; and then centrifuged with 15,000 g of gravity for 10 minutes at 4° C., and supernatant was collected then protein was quantitated with BIO-Rad Protein Dye Reagent™. 20 μg of protein was separated according to sizes thereof with 8% SDS-PAGE, and blotted on PDF (BioRad) membrane with 50V for 12 hours. The blots obtained were blocked with 5% of fat-free milk solution for 1 hour and performed Western blotting with enhanced chemiluminescence (ECL) kit of Amersham Bioscience by using polyclonal anti-PARP (Santa Cruz) as primary antibody and using anti-rabbit IgG (amersham) combined with horse radish peroxidase as secondary antibody.

Figure 6:
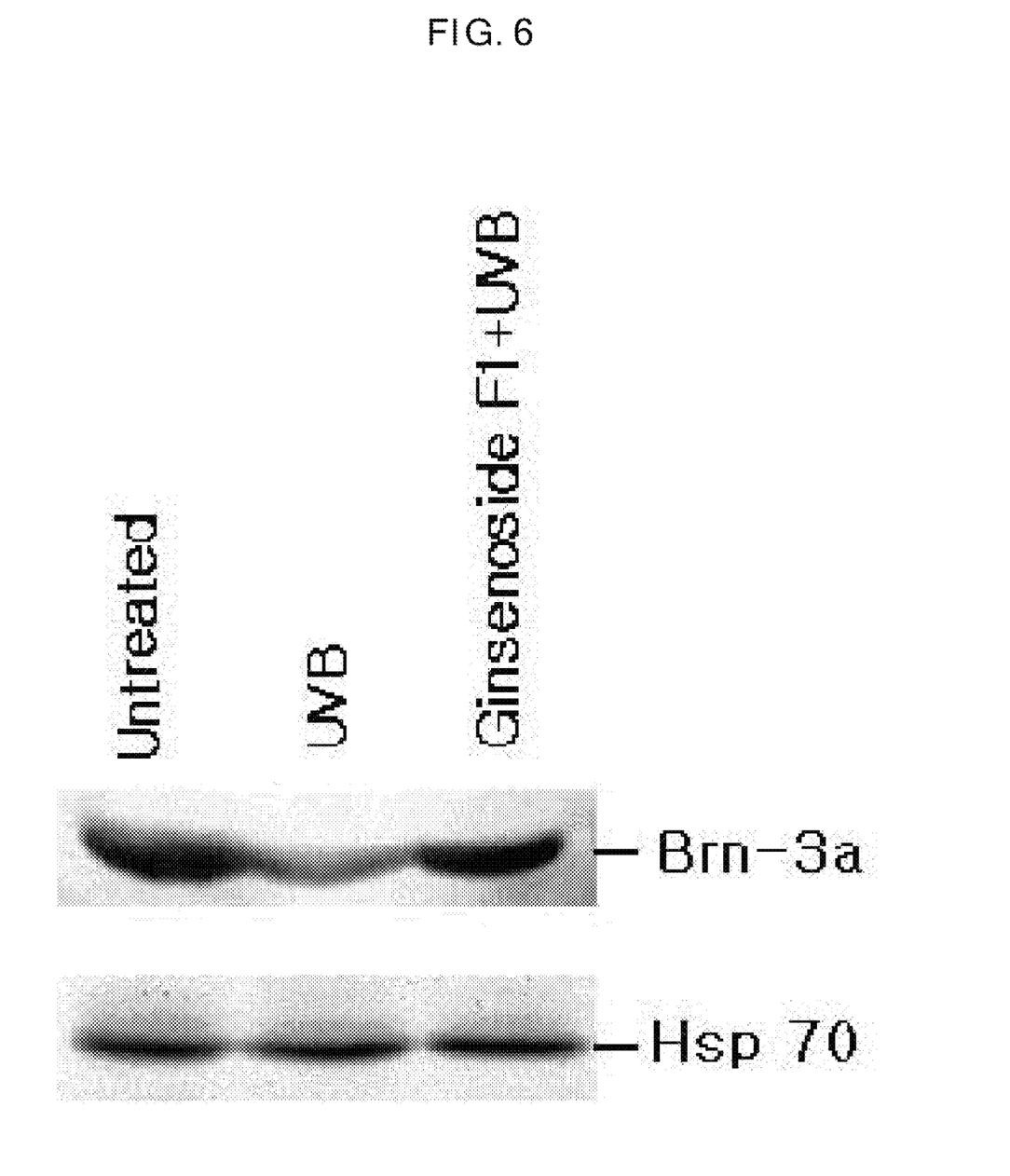
FIG. 6 shows the degrees of the expression of Brn-3a, a transcription factor of Bcl-2, obtained from Western blotting, wherein cells treated with ginsenoside F1 and exposed to ultraviolet radiation were compared with a control untreated with ginsenoside F1. Hsp 70 means that a same amount of protein was used.

The blots reacted were exposed to X-ray Fuji film and developed to observe the degree of protein expression. Bands on the film were scanned with PowerLook 2100 XL (umax) and analyzed with an image-analyzing program of ImageMaster 2D Elite (Amersham Bioscience). The expression of Brn-3a decreased when UVB was radiated, however the expression was recovered when treated with ginsenoside F1. The results are shown in FIG. 6.

As described above, ginsenoside F1 of the present invention inhibits the decrease of Bcl-2 expression caused by ultraviolet radiation to inhibit apoptosis induced from ultraviolet radiation, on the contrary under the high-dose ultraviolet radiation, ginsenoside F1 promotes apoptosis of cell to prevent the cell from developing as a cancer cell.

The invention claimed is:

1. A method of protecting skin from UVB-caused damages comprising administering a composition into a subject in need thereof, the composition consisting of 1-10 μM of isolated and purified ginsenoside F1 as an active component to control expression of Bcl-2 that inhibits apoptosis of a cell, by controlling expression of a transcription factor Brn-3a to maintain a constant level of factor Brn-3a.

2. The method according to claim 1, wherein ginsenoside F1 inhibits apoptosis that is induced by low-dose ultraviolet radiation, by inhibiting decreased expression of Bcl-2.

3. The method according to claim 1, wherein ginsenoisde F1 promotes apoptosis by inducing decreased expression of Bcl-2 under a high dose ultraviolet radiation.

* * * * *